(12) United States Patent
Machan et al.

(10) Patent No.: US 8,834,449 B2
(45) Date of Patent: Sep. 16, 2014

(54) MIXING SYRINGE

(75) Inventors: Lindsay S. Machan, Vancouver (CA); Daniel Gelbart, Vancouver (CA)

(73) Assignee: Ikomed Technologies, Inc. (CA)

(*) Notice: Subject to any disclaimer, the term of this patent is extended or adjusted under 35 U.S.C. 154(b) by 40 days.

(21) Appl. No.: 13/385,627

(22) Filed: Feb. 28, 2012

(65) Prior Publication Data
US 2013/0226148 A1 Aug. 29, 2013

Related U.S. Application Data

(60) Provisional application No. 61/632,263, filed on Jan. 23, 2012.

(51) Int. Cl.
*A61M 5/31* (2006.01)

(52) U.S. Cl.
USPC ............. 604/518; 604/82; 604/90; 604/91; 604/92

(58) Field of Classification Search
USPC ............. 604/82–92, 416, 518; 210/622–623, 210/650
See application file for complete search history.

(56) References Cited

U.S. PATENT DOCUMENTS

| | | | |
|---|---|---|---|
| 2,514,454 A | 7/1950 | Nicholson | |
| 3,493,503 A * | 2/1970 | Mass | 210/778 |
| 3,548,825 A | 12/1970 | Shaw | |
| 3,570,486 A | 3/1971 | Engelsher et al. | |
| 3,606,094 A | 9/1971 | Mills et al. | |
| 3,661,265 A * | 5/1972 | Greenspan | 210/359 |
| 3,724,077 A | 4/1973 | Preston et al. | |
| 3,889,674 A | 6/1975 | Cilento | |
| 4,031,892 A | 6/1977 | Hurschman | |
| 4,041,945 A | 8/1977 | Guiney | |
| 4,116,240 A | 9/1978 | Guiney | |
| 4,412,836 A * | 11/1983 | Brignola | 604/87 |
| 4,435,507 A * | 3/1984 | Stenkvist | 435/262 |
| 4,437,858 A * | 3/1984 | Ty | 604/90 |
| 4,698,299 A | 10/1987 | Janoff et al. | |
| 4,751,921 A * | 6/1988 | Park | 606/93 |
| 4,776,704 A | 10/1988 | Kopunek et al. | |
| 4,981,468 A * | 1/1991 | Benefiel et al. | 604/83 |
| 5,002,537 A | 3/1991 | Hoffman et al. | |
| 5,069,670 A | 12/1991 | Vetter et al. | |
| 5,122,117 A | 6/1992 | Haber et al. | |

(Continued)

FOREIGN PATENT DOCUMENTS

DE 10356335 6/2005
DE 102004055298 5/2006

(Continued)

OTHER PUBLICATIONS

International Search Report and Written Opinion dated May 15, 2013 for PCT/US2013/022561.

*Primary Examiner* — Quynh-Nhu H Vu
(74) *Attorney, Agent, or Firm* — Stoel Rives LLP

(57) ABSTRACT

A movable mixing disc is inserted into a regular syringe. The mixing disc has a small hole covered by a fine screen, allowing only saline solution to get behind the disc. When the plunger of the syringe is pressed, the saline solution emerges from the mixing disc hole as a high velocity jet, stirring up the settled particles. As the ejection continues, the mixing disc is pushed forward by the plunger in order to eliminate any unused volume.

18 Claims, 2 Drawing Sheets

(56) References Cited

U.S. PATENT DOCUMENTS

| | | |
|---|---|---|
| 5,139,490 A | 8/1992 | Vetter et al. |
| 5,244,465 A | 9/1993 | Michel |
| 5,298,023 A | 3/1994 | Haber et al. |
| 5,308,340 A | 5/1994 | Harris |
| 5,320,603 A | 6/1994 | Vetter et al. |
| 5,360,410 A | 11/1994 | Wacks |
| 5,372,029 A | 12/1994 | Brandes |
| 5,435,076 A | 7/1995 | Hjertman et al. |
| 5,501,673 A | 3/1996 | Hjertman et al. |
| 5,514,097 A | 5/1996 | Knauer |
| 5,542,411 A | 8/1996 | Rex |
| 5,549,561 A | 8/1996 | Hjertman et al. |
| 5,549,575 A | 8/1996 | Giambattista et al. |
| 5,554,134 A | 9/1996 | Bonnichsen |
| 5,592,866 A | 1/1997 | Sher |
| 5,626,566 A | 5/1997 | Petersen et al. |
| 5,693,027 A | 12/1997 | Hansen et al. |
| 5,716,338 A | 2/1998 | Hjertman et al. |
| 5,725,500 A | 3/1998 | Micheler |
| 5,725,508 A | 3/1998 | Chanoch et al. |
| 5,785,682 A | 7/1998 | Grabenkort et al. |
| 5,785,692 A | 7/1998 | Attermeier et al. |
| 5,788,670 A | 8/1998 | Reinhard et al. |
| 5,820,602 A | 10/1998 | Kovelman et al. |
| 5,823,998 A | 10/1998 | Yamagata |
| 5,891,087 A | 4/1999 | Ohtani et al. |
| 6,036,675 A | 3/2000 | Thorne et al. |
| 6,106,501 A | 8/2000 | Michel |
| 6,126,646 A | 10/2000 | Hansen et al. |
| 6,203,529 B1 | 3/2001 | Gabriel et al. |
| 6,241,709 B1 | 6/2001 | Bechtold et al. |
| 6,277,097 B1 | 8/2001 | Mikkelsen et al. |
| 6,319,225 B1 | 11/2001 | Sugita et al. |
| 6,331,173 B1 | 12/2001 | Ljungquist |
| 6,419,656 B1 | 7/2002 | Vetter et al. |
| 6,582,404 B1 | 6/2003 | Klitgaard et al. |
| 6,582,408 B1 | 6/2003 | Buch-Rasmussen et al. |
| 6,645,179 B1 | 11/2003 | Ishikawa et al. |
| 6,679,248 B2 | 1/2004 | Stadelhofer |
| 6,793,646 B1 | 9/2004 | Giambattista et al. |
| 6,817,987 B2 * | 11/2004 | Vetter et al. ............... 604/85 |
| 6,899,698 B2 | 5/2005 | Sams |
| 7,081,108 B2 | 7/2006 | Langley et al. |
| 7,101,354 B2 | 9/2006 | Thorne, Jr. et al. |
| 7,402,150 B2 | 7/2008 | Matsumoto et al. |
| 7,686,782 B2 | 3/2010 | Kirchhofer et al. |
| 7,749,200 B2 | 7/2010 | Graf et al. |
| 7,771,398 B2 | 8/2010 | Knight et al. |
| 7,811,263 B2 | 10/2010 | Burren et al. |
| 7,815,598 B2 | 10/2010 | Hommann et al. |
| RE41,956 E | 11/2010 | Klitgaard et al. |
| 7,828,172 B2 | 11/2010 | Stradella et al. |
| 7,850,662 B2 | 12/2010 | Veasey et al. |
| 7,867,202 B2 | 1/2011 | Moser et al. |
| 7,883,490 B2 | 2/2011 | Casey, II et al. |
| 7,918,832 B2 | 4/2011 | Veasey et al. |
| 7,918,833 B2 | 4/2011 | Veasey |
| 7,967,779 B2 | 6/2011 | Bertron et al. |
| 8,002,734 B2 | 8/2011 | Bassarab et al. |
| 8,075,515 B2 | 12/2011 | Matusch |
| 8,092,421 B2 | 1/2012 | Seiferlein et al. |
| 8,092,422 B2 | 1/2012 | Seiferlein et al. |
| 8,096,971 B2 | 1/2012 | Bassarab et al. |
| 8,152,766 B2 | 4/2012 | Karlsson et al. |
| 8,187,233 B2 | 5/2012 | Harms et al. |
| 8,246,577 B2 | 8/2012 | Schrul et al. |
| 8,267,900 B2 | 9/2012 | Harms et al. |
| 8,298,175 B2 | 10/2012 | Hirschel et al. |
| 8,366,680 B2 | 2/2013 | Raab |
| 8,376,993 B2 | 2/2013 | Cox et al. |
| 8,398,593 B2 | 3/2013 | Eich et al. |
| 8,414,541 B2 | 4/2013 | Spofforth |
| 8,439,864 B2 | 5/2013 | Galbraith et al. |
| 2001/0053894 A1 | 12/2001 | Steenfeldt-Jensen et al. |
| 2002/0033367 A1 * | 3/2002 | Prince et al. ............... 210/650 |
| 2002/0165500 A1 | 11/2002 | Bechtold et al. |
| 2002/0173752 A1 | 11/2002 | Polzin |
| 2003/0032935 A1 | 2/2003 | Damiano et al. |
| 2004/0092883 A1 | 5/2004 | Casey et al. |
| 2004/0108339 A1 | 6/2004 | Hansen et al. |
| 2004/0158226 A1 * | 8/2004 | Soo Hoo et al. ............... 604/500 |
| 2004/0186441 A1 | 9/2004 | Graf et al. |
| 2005/0049550 A1 | 3/2005 | Kirchhofer et al. |
| 2005/0154352 A1 | 7/2005 | Gurtner et al. |
| 2005/0177114 A1 | 8/2005 | Michel et al. |
| 2005/0261634 A1 | 11/2005 | Karlsson |
| 2006/0111666 A1 | 5/2006 | Hommann et al. |
| 2006/0178638 A1 | 8/2006 | Reynolds |
| 2006/0178644 A1 | 8/2006 | Reynolds |
| 2006/0254788 A1 | 11/2006 | Bucher |
| 2006/0258988 A1 | 11/2006 | Keitel et al. |
| 2007/0027430 A1 | 2/2007 | Hommann |
| 2007/0060875 A1 | 3/2007 | Bassarab et al. |
| 2007/0060877 A1 | 3/2007 | Bassarab et al. |
| 2007/0129673 A1 | 6/2007 | Bassarab et al. |
| 2007/0163366 A1 | 7/2007 | Jeong et al. |
| 2007/0197975 A1 | 8/2007 | Burren et al. |
| 2007/0270739 A1 | 11/2007 | Kirchhofer et al. |
| 2008/0071226 A1 | 3/2008 | Moser et al. |
| 2008/0126102 A1 | 5/2008 | Shirakawa et al. |
| 2008/0300550 A1 | 12/2008 | Schiller et al. |
| 2009/0137964 A1 | 5/2009 | Enggaard et al. |
| 2009/0157041 A1 | 6/2009 | Pettis et al. |
| 2009/0209920 A1 | 8/2009 | Moller et al. |
| 2009/0247985 A1 | 10/2009 | Melsheimer et al. |
| 2009/0254027 A1 | 10/2009 | Moller |
| 2010/0030551 A1 | 2/2010 | Ark et al. |
| 2010/0036320 A1 | 2/2010 | Cox et al. |
| 2010/0069845 A1 | 3/2010 | Marshall et al. |
| 2010/0082013 A1 | 4/2010 | Braga et al. |
| 2010/0087799 A1 | 4/2010 | Galbraith et al. |
| 2010/0185156 A1 * | 7/2010 | Kanner et al. ............... 604/190 |
| 2010/0262074 A1 | 10/2010 | Seiferlein et al. |
| 2010/0274198 A1 | 10/2010 | Bechtold |
| 2010/0323322 A1 | 12/2010 | Jessop et al. |
| 2010/0327007 A1 | 12/2010 | Fransson et al. |
| 2011/0060274 A1 | 3/2011 | Kuhn |
| 2011/0100921 A1 * | 5/2011 | Heinrich ............... 210/670 |
| 2011/0152784 A1 | 6/2011 | Veasey et al. |
| 2011/0152822 A1 | 6/2011 | Drunk et al. |
| 2011/0196310 A1 | 8/2011 | Cronenberg |
| 2011/0201999 A1 | 8/2011 | Cronenberg et al. |
| 2011/0224622 A1 | 9/2011 | Karlsson |
| 2011/0230827 A1 | 9/2011 | Mori et al. |
| 2012/0041366 A1 | 2/2012 | Fayyaz et al. |
| 2012/0046613 A1 | 2/2012 | Plumptre |
| 2012/0078171 A1 | 3/2012 | Seiferlein et al. |
| 2012/0078195 A1 | 3/2012 | Harms et al. |
| 2012/0089100 A1 | 4/2012 | Veasey et al. |
| 2012/0095413 A1 | 4/2012 | Nzike et al. |
| 2012/0118139 A1 | 5/2012 | Seiferlein et al. |
| 2012/0130316 A1 | 5/2012 | Boyd et al. |
| 2012/0136298 A1 | 5/2012 | Bendix et al. |
| 2012/0136306 A1 | 5/2012 | Bartha |
| 2012/0136315 A1 | 5/2012 | Wieselblad et al. |
| 2012/0172816 A1 | 7/2012 | Boyd et al. |
| 2012/0209171 A1 | 8/2012 | Vedrine et al. |
| 2012/0283646 A1 | 11/2012 | Kouyoumjian et al. |
| 2012/0289929 A1 | 11/2012 | Boyd et al. |
| 2012/0310168 A1 | 12/2012 | Plumptre et al. |
| 2013/0018327 A1 | 1/2013 | Dasbach et al. |
| 2013/0046245 A1 | 2/2013 | Raab et al. |
| 2013/0053789 A1 | 2/2013 | Harms et al. |
| 2013/0096513 A1 | 4/2013 | Smith |
| 2013/0131605 A1 | 5/2013 | Hiles |
| 2013/0190719 A1 | 7/2013 | Smith et al. |
| 2013/0211326 A1 | 8/2013 | Dashbach et al. |
| 2013/0218098 A1 | 8/2013 | Chung |
| 2013/0245562 A1 | 9/2013 | Kouyoumjian et al. |
| 2013/0253433 A1 | 9/2013 | Senior et al. |

(56) References Cited

U.S. PATENT DOCUMENTS

FOREIGN PATENT DOCUMENTS

| | | |
|---|---|---|
| EP | 0513128 | 11/1992 |
| EP | 0829268 | 3/1998 |
| EP | 1923085 | 5/2008 |
| EP | 1974761 | 10/2008 |
| EP | 2263721 | 12/2010 |
| EP | 2263722 | 12/2010 |
| EP | 2514454 | 10/2012 |
| FR | 2847887 | 6/2004 |
| KR | 1020110041826 | 4/2011 |
| WO | WO 92/04926 | 4/1992 |
| WO | WO 2006/079898 | 8/2006 |
| WO | WO 2009/141005 | 11/2009 |
| WO | WO 2010/003262 | 1/2010 |
| WO | WO 2010/105376 | 9/2010 |
| WO | WO 2011/131775 | 10/2011 |
| WO | WO 2011/131779 | 10/2011 |
| WO | WO 2011/154488 | 12/2011 |
| WO | WO 2012/010832 | 1/2012 |
| WO | WO 2012/072568 | 6/2012 |
| WO | WO 2012/085017 | 6/2012 |
| WO | WO 2012/128699 | 9/2012 |
| WO | WO 2012/152666 | 11/2012 |
| WO | WO 2013/033227 | 3/2013 |
| WO | WO 2013/043861 | 3/2013 |

* cited by examiner

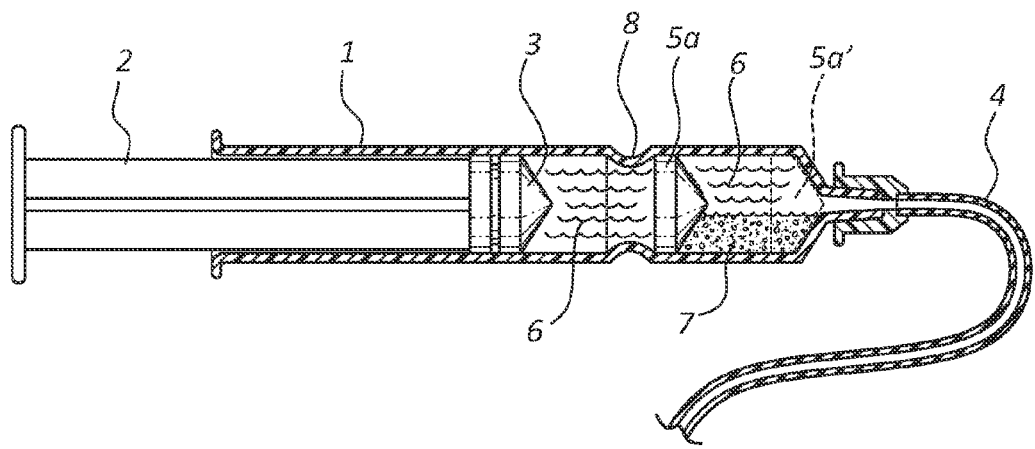
FIG. 1
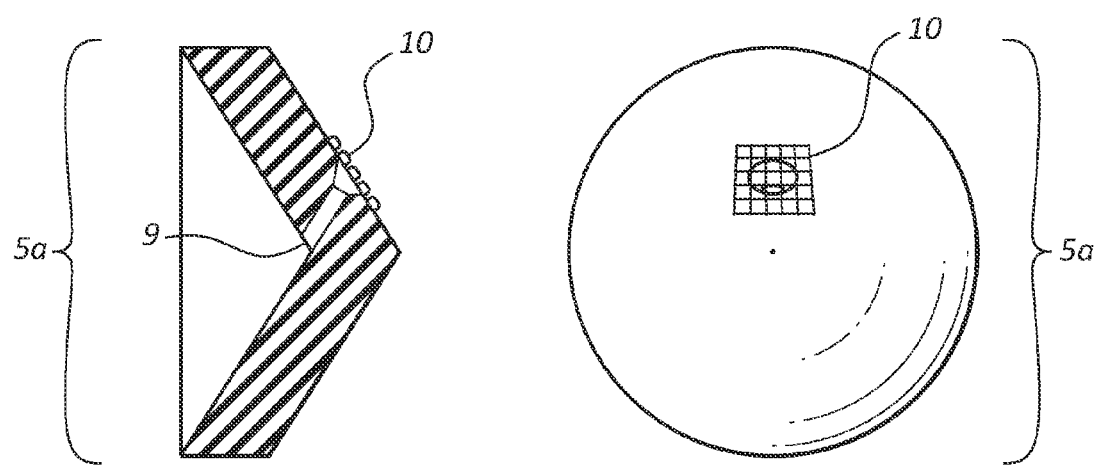
FIG. 2A  FIG. 2B

MIXING SYRINGE

The present application claims the benefit under 35 U.S.C. §119(e) of U.S. Provisional Application No. 61/632,263 filed on Jan. 23, 2012.

FIELD OF THE INVENTION

The invention is in the medical field, and is particularly useful in percutaneous procedures such as embolization.

BACKGROUND OF THE INVENTION

In certain medical procedures, such as blood vessel embolization, it is desired to inject particles into the body. The procedure is a minimally invasive alternative to surgery. The purpose of embolization is to prevent blood flow to an area of the body, which effectively can shrink a fibroid, such as a uterine fibroid. It can also shrink a tumour or block an aneurysm. It is typically done by injecting blocking particles into a blood vessel.

The procedure is carried out as an endovascular procedure by a radiologist in an interventional suite. It is common for most patients to have the treatment carried out with little or no sedation, although this depends largely on the organ to be embolized.

Access to the organ in question is acquired by means of a guidewire and catheter. The position of the correct artery or vein supplying the undesired tissue in question is located by X-Ray images. These images are then used as a map for the radiologist to gain access to the correct vessel by selecting an appropriate catheter and or wire, depending on the shape of the surrounding anatomy The blocking particles are mixed into a saline solution, sometimes a contrast agent is added (to make the solution opaque to X-Rays). The blocking particles have to be of certain sizes, typically between 0.1 mm to 1 mm, in order to block the blood vessel at the right diameter. Such particles tend to settle very quickly out of the solution as they are heavier than water, causing an uneven concentration of particles during the injection. The settling occurs in as little as a few seconds. It is inconvenient to keep shaking the syringe used for injection, as the whole process is performed in a few seconds and the doctor has to concentrate on injecting the correct amount. It is desired to have a syringe that can keep the particles uniformly dispersed in the saline solution regardless of delays in the injection process or speed of the injection. Since the syringes used are low cost disposable items, it is desired that the device used to keep the particles uniformly dispersed will also be very low cost and disposable. The ideal mixing syringe needs the following attributes:

A. Ability to be re-filled multiple times during a procedure. This rules out any single-use designs, typically using the rupturing of a membrane to allow mixing.
B. Generate a strong mixing action, preferable by creating a vortex in the mixture.
C. Use the minimum modification to a standard syringe.

Prior art mixing syringes, such as disclosed in U.S. Pat. No. 7,883,490 are designed to mix together two materials stored separately in two compartments. They are not designed to stir up a pre-mixed solution. Prior art syringes designed to stir-up embolization mixtures, such as disclosed in US2009/0247985, are needlessly complex. Also, many of the prior art mixing syringes are not designed to be filled with the pre-mixed solution just before use. This is required during embolization, as the correct volume and ratio of saline, particles and contrast agent has to be customized to the procedure by the doctor. The current invention acts as a regular syringe, allowing filling and injecting at any time, but it keeps the solution stirred up during injection. Similar to a regular syringe, it can be re-used several times during a procedure, if more particles have to be injected. The invention can be manufactured out of a regular syringe, which is a very low cost item.

SUMMARY OF THE INVENTION

A movable mixing disc is inserted into a regular syringe. The mixing disc has a small hole covered by a fine screen, allowing only saline solution to get behind disc. When the plunger of the syringe is pressed, the saline solution emerges from the mixing disc hole as a high velocity jet, stirring up the settled particles. As the ejection continues, the mixing disc is pushed forward by the plunger in order to eliminate any unused volume.

BRIEF DESCRIPTION OF THE DRAWINGS

FIG. 1 shows a general view of the invention.
FIG. 2A shows a cross section of the mixing disc.
FIG. 2B shows a front view of the mixing disc of FIG. 2A.

DETAILED DESCRIPTION

Figure 3:
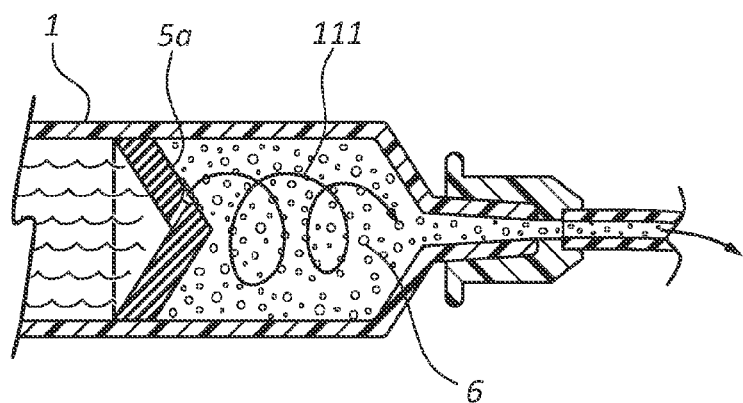
FIG. 3 shows the action of the mixing disc.

Referring now to FIG. 1, the mixing syringe is a regular syringe with the addition of a mixing disc. A syringe 1 includes a plunger 2 and a seal 3 in order to eject the liquid 6 via tube 4. A piston-like mixing disc 5a is added into the syringe. The initial position of disc 5a is shown as 5a', with plunger seal 3 touching disc 5a. As liquid and particles are sucked into syringe 1, seal 3 moves farther from disc 5a to create a vacuum. Disc 5a moves as well, until stopped by slight ridge 8. The size of the ridge is exaggerated in FIG. 1 for clarity. It only needs to reduce the inside diameter by about 0.2-0.3 mm. Flexible seal 3 easily passes over such a ridge. The particles 7 are sucked into the syringe via tube 4 and quickly settle as shown in FIG. 1. The particles do not accumulate in the section between plunger seal 3 and disc 5a as disc 5a includes a filter with pore sizes smaller than the particles. This is shown in FIGS. 2A and 2B. Disc 5a has one or more holes 9 covered by filter mesh 10. It is desired to chamfer hole 9 under screen 10 to increase the effective area of the screen. The screen can also be mounted as a flexible flap, being pushed out of the way during ejection of the fluid. The conical shape of disc 5a is matched to the shape of the conical seal 3 and the conical tip of the syringe. This eliminates trapped fluid between the seal 3 and the syringe outlet at the end of the stroke. The conical shape of disc 5a also aids the removal of any trapped air bubbles, as they float to the top of disc 5a and escape when syringe is held vertically. As plunger 3 is moved towards disc 5a the liquid 6 is ejected via hole 9 at a high velocity, mixing up particles 7 and liquid 6. This is shown in FIG. 3.

From the moment seal 3 touches disc 8 the disc is pushed forward towards the tube 4 until the syringe is empty and disc 5a is in position 5a'. The operation can now be repeated, if desired.

It is desirable to make hole 9 at an angle to the axis of the syringe in order to create a vortex 111. An even more effective vortex 111 can be created if hole 9 is molded as a curved arc, both in the plane of the drawing and also in the plane perpendicular to the drawing.

Disc 5a can be molded in one piece, including screen 10. Alternatively, screen 10 can be bonded to molded disc 5a. The fit between disc 5a and bore of syringe 1 is not critical as the particles are relatively large. It was found out that for best results the diameter of disc 5a should be 0.1-0.2 mm smaller than the inside diameter of syringe 1.

While the example given is for embolization, the invention can be used to mix and two components, including two liquids.

Figures 4A, 4B:
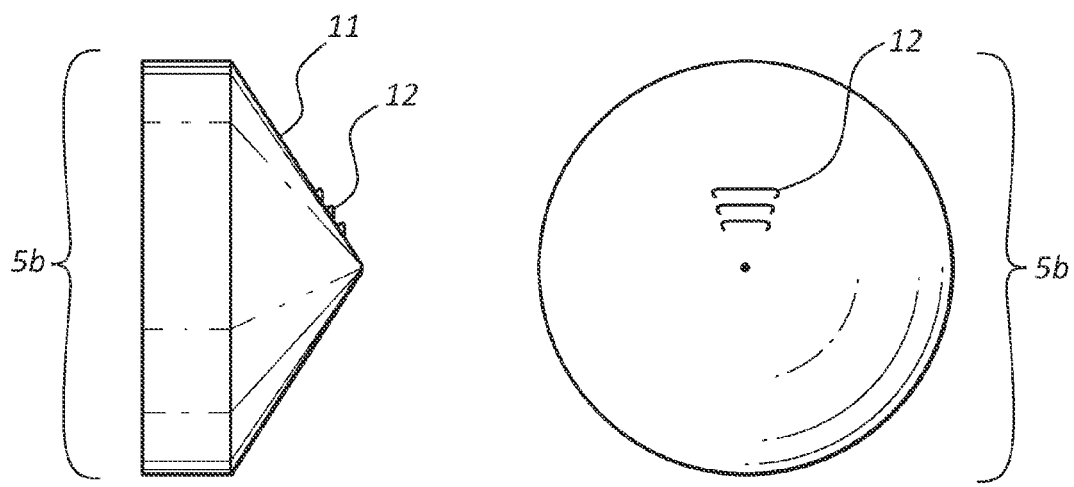
FIG. 4A is a cross section of a mixing disc stamped out of sheet metal.
FIG. 4B is a front view of the mixing disc of FIG. 4A.

The disc 5 can also be made out of pressed sheet metal 11. This is shown as disc 5b in FIGS. 4A and 4B. In this case hole 9 and screen 10 are replaced by miniature stamped louvers 12 (similar to a miniature venetian blind) acting both as a screen and as a flow director. Recommended material is type 316L stainless steel or aluminum, with thickness between 0.1 to 0.3 mm. The thin wall allows seal 3 to enter into the hollow disc and squeeze out all the liquid.

In order to eliminate the need of molding custom syringes it was found out that the slight ridge 8 can be formed in existing syringes by briefly heating up the area of ridge 8 and pressing the walls in slightly, using a split ring slightly smaller than the outside diameter of the syringe. Other ways of creating a ridge without molding is pressing into the syringe a thin walled ring, held by friction.

Figure 5:
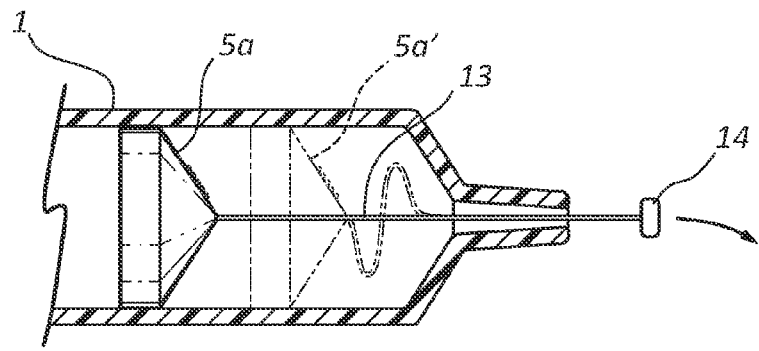
FIG. 5 shows a version of the invention not requiring modifications to the syringe.

If desired the invention can be manufactured out of a standard disposable syringe, without any modifications. The movable disc 5a is attached to the outlet side of the syringe with a short string that only allows it to move a limited distance. The string 13 is bonded by heat to the syringe or uses an anchor 14. This is shown in FIG. 5.

In operation tube 4 is first inserted into a mixing bowl where the ingredients are mixed together. The mixture is sucked into the syringe. After filling the syringe is held vertically to help trapped air escape and plunger moved to expel all air. Afterwards tube 4 is moved to the catheter or needle used for the procedure and mixture is injected.

An additional improvement in mixing is to adjust the density of particles 7 to match the density of liquid 6, typically a saline solution with a density around 1. since the materials used to make particles 7 (plastic, glass or ceramic) have a density greater than 1, they have to be made hollow. The technology of manufacturing small hollow spheres, known as micro-balloons, is well known and many polymers as well as glasses are commercially available in micro-balloon form. One supplier is Henkel (http://www.henkelna.com/cps/rde/xchg/henkel_us/hs.xsl/brands-1556.htm?iname=Dualite%25C2%25AE&countryCode=us&BU=industrial&parentredDotUID=0000000GFR&redDotUID=0000000GFR&brand=000000QTQE Both ideas can be combined: micro-balloon shaped polymer or glass spheres with a density around 1 can be dispensed from a syringe with a mixing disc.

What is claimed is:

1. A syringe configured to contain a mixture of a liquid and solid particles, the syringe comprising:
   a mixing disc comprising a hole that defines a flow path, wherein the mixing disc is configured to:
      move along a portion of a longitudinal axis of the syringe,
      generate a liquid jet for mixing the liquid and the solid particles when liquid is advanced through the hole during ejection of the mixture; and
      prevent the solid particles from passing through the mixing disc;
   wherein a portion of the flow path is not parallel to the longitudinal axis of the syringe.

2. The syringe as in claim 1, further comprising
   a syringe body; and
   a plunger that is configured to move along a movement range within the syringe body;
   wherein the mixing disc is free to move inside the syringe body along a portion of the movement range of the plunger.

3. The syringe as in claim 1, further comprising a syringe body and a plunger, wherein the mixing disc is free to move inside syringe over a limited range, the range being limited by a ridge inside the syringe body.

4. The syringe as in claim 1, wherein the mixing disc comprises molded plastic.

5. The syringe as in claim 1, wherein the mixing disc comprises pressed thin metal.

6. The syringe as in claim 1, wherein the syringe comprises a string bonded to an unmodified disposable syringe.

7. The syringe as in claim 1, wherein the solid particles comprise hollow particles having a density substantially matched to the density of the liquid.

8. The syringe as in claim 1, wherein the mixing disc is shaped to minimize the volume of trapped liquid in the syringe.

9. A syringe comprising:
   a cylindrical body;
   a plunger configured to be disposed within the cylindrical body;
   an outlet positioned at a distal end of the cylindrical body; and
   a movable disc disposed between the plunger and the outlet, the movable disc configured to:
      move along a portion of a longitudinal axis of the cylindrical body in response to a fluidic force acting on the movable disc; and
      create a jet of liquid when the syringe contains a liquid and the plunger is advanced to eject the liquid, the movable disc comprising a screen having pore sizes smaller than particles configured to be mixed with the liquid;
   wherein the movable disc comprises a hole that defines a flow path and the screen is configured to cover the hole, and a portion of the flow path is not parallel to the longitudinal axis of the syringe.

10. The syringe as in claim 9, wherein the hole is slanted and the jet is created by the slanted-hole in the movable disc.

11. The syringe as in claim 9, wherein motion of the movable disc is restricted by a ridge inside the syringe.

12. The syringe as in claim 9, wherein the movable disc is shaped to minimize the volume of trapped liquid in the syringe.

13. The syringe as in claim 9, wherein the syringe comprises a string bonded to an unmodified disposable syringe.

14. The syringe of claim 9, wherein:
   the syringe is configured to generate the jet of fluid by advancing the plunger such that liquid passes through the hole in the movable disc; and
   the screen is configured to cover the hole as the plunger is being withdrawn and to be displaced by the jet of liquid as the plunger is being advanced.

15. A method of displacing a mixture of a liquid and solid particles using a syringe, the method comprising:
   disposing a mixture of the liquid and solid particles within the syringe;
   separating a portion of the liquid from the mixture by retracting a plunger within a syringe body to suck the liquid through a screen having pore sizes smaller than the particles, wherein the screen is coupled to a movable disc that is configured to move within the syringe body along a portion of a longitudinal axis of the syringe body in response to a fluidic force acting on the movable disc; and ejecting the separated liquid into the mixture to create a flow pattern in the mixture, the flow pattern configured to prevent the solid particles from settling;

where the flow pattern configured to prevent solid particles from setting is generated by the election of the separated liquid through a hole, wherein the hole defines a flow path and a portion of the flow path is not parallel to the longitudinal axis of the syringe body.

16. The method as in claim 15, wherein motion of the movable disc is restricted by a ridge inside the syringe.

17. The method as in claim 15, wherein the syringe comprises a string bonded to an unmodified disposable syringe.

18. A method of displacing a mixture of a liquid and solid particles using a syringe, the method comprising:

disposing a mixture of liquid and solid particles within the syringe;

separating a portion of the liquid from the mixture by sucking it through a louvered hole with openings smaller than the particles, the louvered hole coupled to a movable disc inside the syringe; and ejecting the separated liquid into the mixture to create a flow pattern in the mixture, the flow pattern configured to prevent the solid particles from settling;

wherein the louvered hole defines a flow path such that a portion of the flow path is not parallel to the longitudinal axis of the syringe.

\* \* \* \* \*